United States Patent
Denton et al.

(10) Patent No.: US 12,148,508 B2
(45) Date of Patent: Nov. 19, 2024

(54) PREDICTIVE ENGINE MAINTENANCE APPARATUSES, METHODS, SYSTEMS AND TECHNIQUES

(71) Applicant: Cummins Inc., Columbus, IN (US)

(72) Inventors: Ryan E. Denton, Franklin, IN (US); Xinjian Xue, Carmel, IN (US); Corey W. Trobaugh, Columbus, IN (US); Anthony Joseph Huth, Cincinnati, OH (US)

(73) Assignee: Cummins Inc., Columbus, IN (US)

( * ) Notice: Subject to any disclaimer, the term of this patent is extended or adjusted under 35 U.S.C. 154(b) by 333 days.

(21) Appl. No.: 17/664,700

(22) Filed: May 24, 2022

(65) Prior Publication Data

US 2022/0284988 A1 Sep. 8, 2022

Related U.S. Application Data

(63) Continuation of application No. PCT/US2020/061917, filed on Nov. 24, 2020.

(60) Provisional application No. 62/940,434, filed on Nov. 26, 2019.

(51) Int. Cl.
*G16B 40/20* (2019.01)
*G06F 18/214* (2023.01)
*G06N 5/01* (2023.01)
*G06N 5/04* (2023.01)

(52) U.S. Cl.
CPC .......... *G16B 40/20* (2019.02); *G06F 18/214* (2023.01); *G06N 5/01* (2023.01); *G06N 5/04* (2013.01)

(58) Field of Classification Search
CPC .......... G06N 5/01; G06N 5/04; G06F 18/214; G16B 40/20; G06Q 10/20
See application file for complete search history.

(56) References Cited

U.S. PATENT DOCUMENTS

| | | |
|---|---|---|
| 521,704 A | 6/1894 | Davis |
| 3,981,584 A | 9/1976 | Guymer |
| 7,581,434 B1 | 9/2009 | Discenzo |
| 7,917,307 B2 | 3/2011 | Bolt |
| 9,714,931 B2 | 7/2017 | Prabhu et al. |
| 9,897,582 B2 | 2/2018 | Jean et al. |

(Continued)

OTHER PUBLICATIONS

International Search Report and Written Opinion, PCT Appln. No. PCT/US20/061917, Feb. 21, 2021, p. 10.

(Continued)

*Primary Examiner* — An H Do
(74) *Attorney, Agent, or Firm* — Taft, Stettinius & Hollister LLP

(57) ABSTRACT

A method includes inputting used oil analysis data to a pre-trained predictive model, the used oil analysis data including values quantifying a plurality of chemical components measured in a sample of used oil taken from an engine under analysis, determining a probability of at least one fail code with the pre-trained predictive model in response to the used oil analysis data, the at least one fail code corresponding to one of a plurality of predetermined engine failure types, providing the at least one fail code and the probability of the at least one fail code to an expert system, performing with the expert system a root cause analysis of the at least one fail code determine a root cause indicating a preventative maintenance action, and performing the predictive maintenance action on the engine under analysis.

20 Claims, 4 Drawing Sheets

(56) References Cited

U.S. PATENT DOCUMENTS 10,151,739 B2 12/2018 Jean
2018/0299375 A1 10/2018 Young et al.

OTHER PUBLICATIONS

Wakiru, James M. et al. "A review on Lubricant Condition Monitoring Information Analysis for Maintenance Decision Support", Mechanical Systems and signal Processing, Elsevier Amsterdam, NL, vol. 118, Aug. 25, 2018, pp. 108-132.

Input Oil Analysis Data

| Soot = 4 | Kv100 = 19 |
|---|---|
| Al = 58 | Cr = 11 |
| Cu = 61 | Fe = 159 |
| Pb = 228 | Sn = 6 |
| Si = 42 | Na = 593 |
| K = 1632 | |

Predicted Fail Codes and Probability of Occurrence

| Fail Code | Probability |
|---|---|
| FC008 | 0.977 |
| FC122 | 0.902 |
| FC305 | 0.883 |
| FC287 | 0.826 |
| FC401 | 0.808 |

Fail Code and Related Fail Codes Based on Recommendation Model

| Fail Code | Related FC1 | Related FC2 | Related FC3 | Related FC4 | Related FC5 |
|---|---|---|---|---|---|
| FC008 | FC153 | FC422 | FC371 | FC098 | FC267 |

Fail Code, Cause, and Adjacent Fail Codes Based on Expert System

| Fail Code | Description | Potential Cause | Cause 1 | Cause 2 |
|---|---|---|---|---|
| FC008 | EGR Cooler Core | Potential Coolant Contamination | Coolant Contamination | Broken Oil/ Corrosion |

Root Cause(s) and Adjacent Fail Codes

| Root Cause | ADJ 1 | ADJ 2 | ADJ 3 | ADJ 4 | ADJ 5 |
|---|---|---|---|---|---|
| Coolant Contamination | FC008 | FC433 | FC374 | FC083 | FC122 |
| Broken Oil/ Corrosion | FC008 | FC401 | FC288 | -- | -- |

Fig. 4

PREDICTIVE ENGINE MAINTENANCE APPARATUSES, METHODS, SYSTEMS AND TECHNIQUES

RELATED APPLICATIONS

The present application is a continuation of International Application No. PCT/US2020/061917 filed on Nov. 24, 2020, which claims priority to and the benefit of U.S. Application No. 62/940,434, filed Nov. 26, 2019 the disclosures of which are hereby incorporated by reference.

BACKGROUND

The present disclosure relates to predictive engine maintenance apparatuses, methods, systems, and techniques. Predictive engine maintenance apparatuses, methods, systems, and techniques seek to predict future engine failure events (e.g., malfunction or complete failure of one or more engine systems or components requiring maintenance, repair, and/or replacement to restore engine functionality) and to identify and provide maintenance, repair or replacement before the occurrence of the future engine failure events. A number of proposals for predictive engine maintenance apparatuses, methods, systems, and techniques have been made; however, existing proposals suffer from a number of drawbacks, shortcomings, and unrealized potential. There remains a substantial need for the unique apparatuses, methods, systems, and techniques disclosed herein.

DISCLOSURE OF ILLUSTRATIVE EMBODIMENTS

For the purposes of clearly, concisely, and exactly describing illustrative embodiments of the present disclosure, the manner, and process of making and using the same, and to enable the practice, making and use of the same, reference will now be made to certain exemplary embodiments, including those illustrated in the figures, and specific language will be used to describe the same. It shall nevertheless be understood that no limitation of the scope of the invention is thereby created and that the invention includes and protects such alterations, modifications, and further applications of the exemplary embodiments as would occur to one skilled in the art.

SUMMARY OF THE DISCLOSURE

One embodiment is a unique predictive engine maintenance process. Another embodiment is a unique predictive engine maintenance system. Predictive maintenance systems and processes according to the present disclosure may comprise system features and process operations pertaining to data preparation, classification modeling, recommendation modeling, expert system analytics, and web-enabled user interface aspects providing predictive maintenance capability for an engine under evaluation. Further embodiments, forms, objects, features, advantages, aspects, and benefits shall become apparent from the following description and drawings.

BRIEF DESCRIPTION OF THE DRAWINGS

FIG. 4 is an illustration of certain aspects of an example user interface for a predictive maintenance system.

DETAILED DESCRIPTION OF ILLUSTRATIVE EMBODIMENTS

Figure 1:
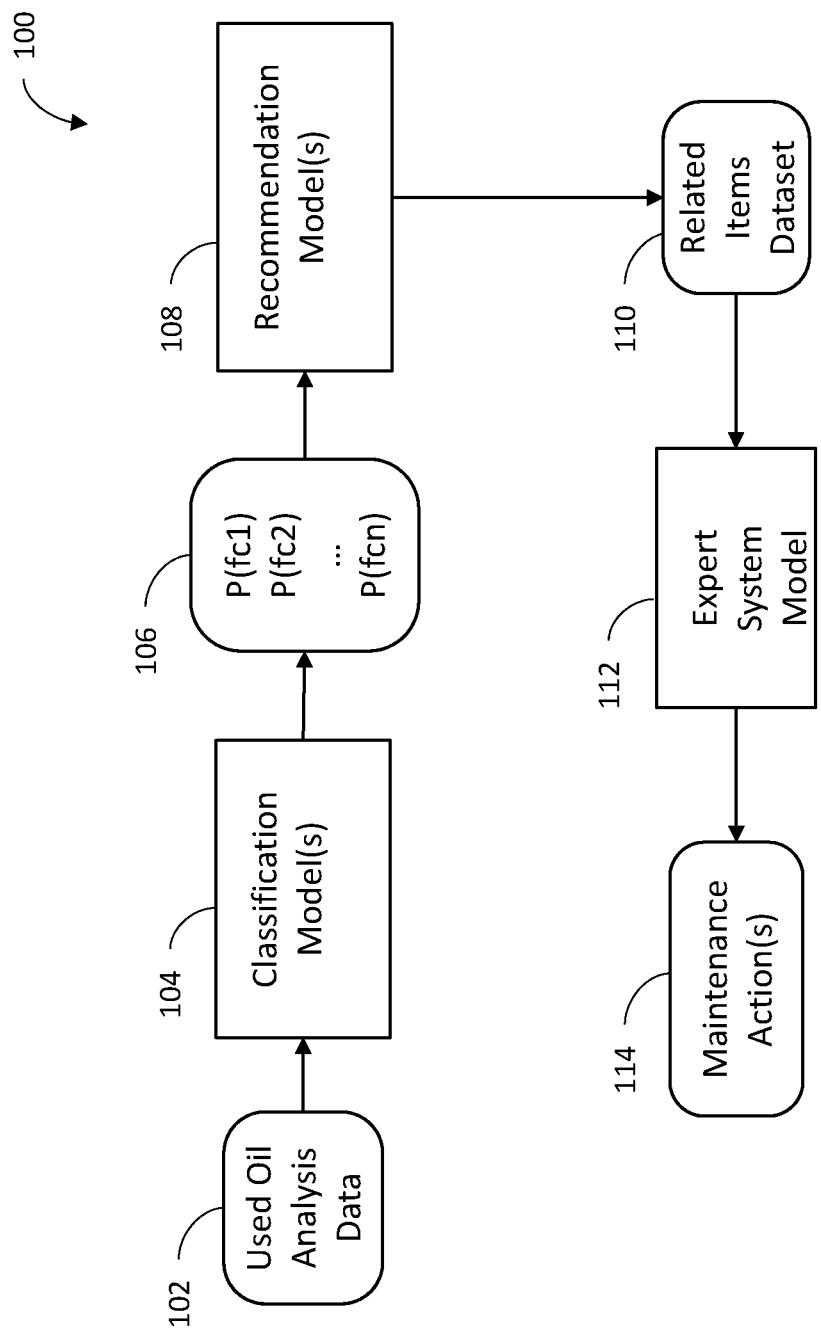
FIG. 1 is a schematic diagram illustrating certain aspects of an example predictive maintenance system.

With reference to FIG. 1, there are illustrated certain aspects of a predictive maintenance system 100 according to one example embodiment. System 100 includes a combination of components including one or more classification model(s) 104, recommendation model(s) 108, and expert system 112. Each of these components, as well as other components of system 100, may be implemented one or more computer systems comprising one or more computers specially configured in accordance with the techniques of the present disclosure to provide the configurations and functionalities described herein. In certain forms, one or more of these components, as well as other components of system 100, may be provided in a web-accessible cloud computing platform, one or more dedicated computing systems such as a local computing system of a maintenance facility, or distributed in part in a web-accessible cloud computing platform and in part in one or more dedicated computing systems.

In system 100, used oil analysis data 102 are input to and received by classification model(s) 104. The used oil analysis data 102 includes values quantifying a plurality of measured attributes of a sample of used oil taken from an engine under analysis by predictive maintenance system 100. Examples of such measured attributes include measurements of viscosity (e.g., kinematic viscosity at 40° C., 100° C. or other predetermined temperatures), soot content, Aluminum (Al) content, Chromium (Cr) content, Copper (Cu) content, Iron (Fe) content, Lead (Pb) content, Tin (Sn) content, Nickel (Ni) content, Silicon (Si) content, Sodium (Na) content, Potassium (K) content, as well as additional and alternate values indicating for other physical, elemental and/or chemical attributes, components, or properties measured in a sample of used oil taken from an engine under analysis by predictive maintenance system 100. Certain embodiments preferably utilize a set of measured attributes comprising measurements of viscosity and one or more compositional contents selected from the group consisting of soot content, Al content, Cr content, Cu content, Fe content, Pb content, Sn content, Ni content, Si content, Na content, and K content. Certain embodiments preferably utilize a set of measured attributes selected from the group consisting of measurements of viscosity, soot content, Al content, Cr content, Cu content, Fe content, Pb content, Sn content, Ni content, Si content, Na content, and K content. Certain embodiments preferably utilize a set of measured attributes consisting of measurements of viscosity, soot content, Al content, Cr content, Cu content, Fe content, Pb content, Sn content, Ni content, Si content, Na content, and K content.

The measurements of compositional contents to provide used oil analysis data 102 may be performed using optical emission spectroscopy (OES) techniques, such as rotating disc electrode optical emission spectroscopy (RDE-OES) or inductively coupled plasma optical emission spectroscopy (ICP-OES), microscopy-based instruments, such as scanning electron microscopy/energy dispersive x-ray analysis (SEM/EDX), or other compositional content. It shall be further appreciated that the measurements of compositional contents may be expressed in terms of fractions or percentages or in absolute terms such as parts-per-million (ppm), parts-per-billion (ppb), other parts-per notations, or other absolute mass-based, weight-based, or volume-based terms.

Classification model(s) 104 are an example of components which are pre-trained prior to receiving used oil analysis data 102 using one or more machine learning techniques such as the techniques described herein below in connection with FIG. 2. Classification model(s) 104 determine and output one or more fail code probabilities 106 (denoted P(fc1), P(fc2) . . . P(fcn) in FIG. 2) by performing a classification operation in response to used oil analysis data 102 and their pre-trained attributes of classification model(s) 104. In certain forms, the classification operation may be a two-class classification. In other forms, the classification operation may be a higher-order multi-class classification. Each of the one or more fail code probabilities indicates a probability that a predetermined unique engine failure event, such as a failure of particular engine component(s) or particular failure type(s), will occur before a future predetermined time, for example, before the next scheduled oil change or other scheduled maintenance for the engine under analysis by system 100. In certain embodiments, classification model(s) 104 preferably include a plurality of classification models selected during machine learning model training, for example, as described below in connection with FIG. 2. The plurality of classification models may represent those classifications for which a minimum probability threshold or criterion was established during training. The one or more fail code probabilities 106 are input to and received by a recommendation model 108.

Recommendation model 108 is an example of components which are pre-trained prior to receiving used oil analysis data 102 using one or more machine learning techniques such as the techniques described below in connection with FIG. 2. Recommendation model 108 determines and outputs a related items dataset 110 in response to fail code probabilities 106 and its pre-trained attributes. Related items dataset 110 includes a set of one or more fail codes that are related to a given one of the fail code probabilities 106, for example, by a causal or correlational relationship. Recommendation model 108 is configured to perform an assessment to identify fail codes that are adjacent to the fail code corresponding to one of the one or more fail code probabilities 106 which are input to and received by a recommendation model 108. In certain forms, the assessment may generate related items using techniques such as collaborative filtering information from prior training and may continue learning after the initial training. Related items dataset 110 is input to and received by expert system 112.

Expert system 112 is an artificial intelligence-based system configured to emulate the decision-making of human experts. Expert system 112 is configured to identify root causes of the fail codes in the related items dataset 110 using an inference engine which operates on a knowledge base represented principally by a ruleset of if-then rules rather than through a conventional algorithm. Expert system 112 may be pre-trained and configured in accordance with the techniques described below in connection with FIG. 2. Expert system 112 determines and outputs a maintenance action(s) dataset 114 in response to related items dataset 110 and its pre-trained attributes. Maintenance action(s) dataset 114 defines one or more maintenance actions in terms of root causes indicating failure, damage, or degradation to one or more particular components of the engine under analysis by predictive maintenance system 100 which are then maintained, repaired, or replaced via execution of the maintenance actions.

System 100 is an example of a machine learning system according to the present disclosure including at least three machine learning model components or layers. In the example of system 100, the provision of at least three machine learning model components (i.e., classification model(s) 104, recommendation model(s) 108, and expert system model 112) which are individually trained to model separate aspects of an overall machine learning-based maintenance prediction system (i.e., classification of used oil analysis data 102 to determine one or more fail code probabilities 106, determination of one a related items dataset 110 including one or more related fail codes in response to the one or more fail code probabilities 106, and determination of a maintenance action(s) dataset 114 in response to related items dataset 110, by classification models(s) 104, recommendation model(s) 108, and expert system model 112, respectively) provides a number of unanticipated benefits relative to other approaches including those respecting accuracy, reliability, speed, trainability.

Figure 2:
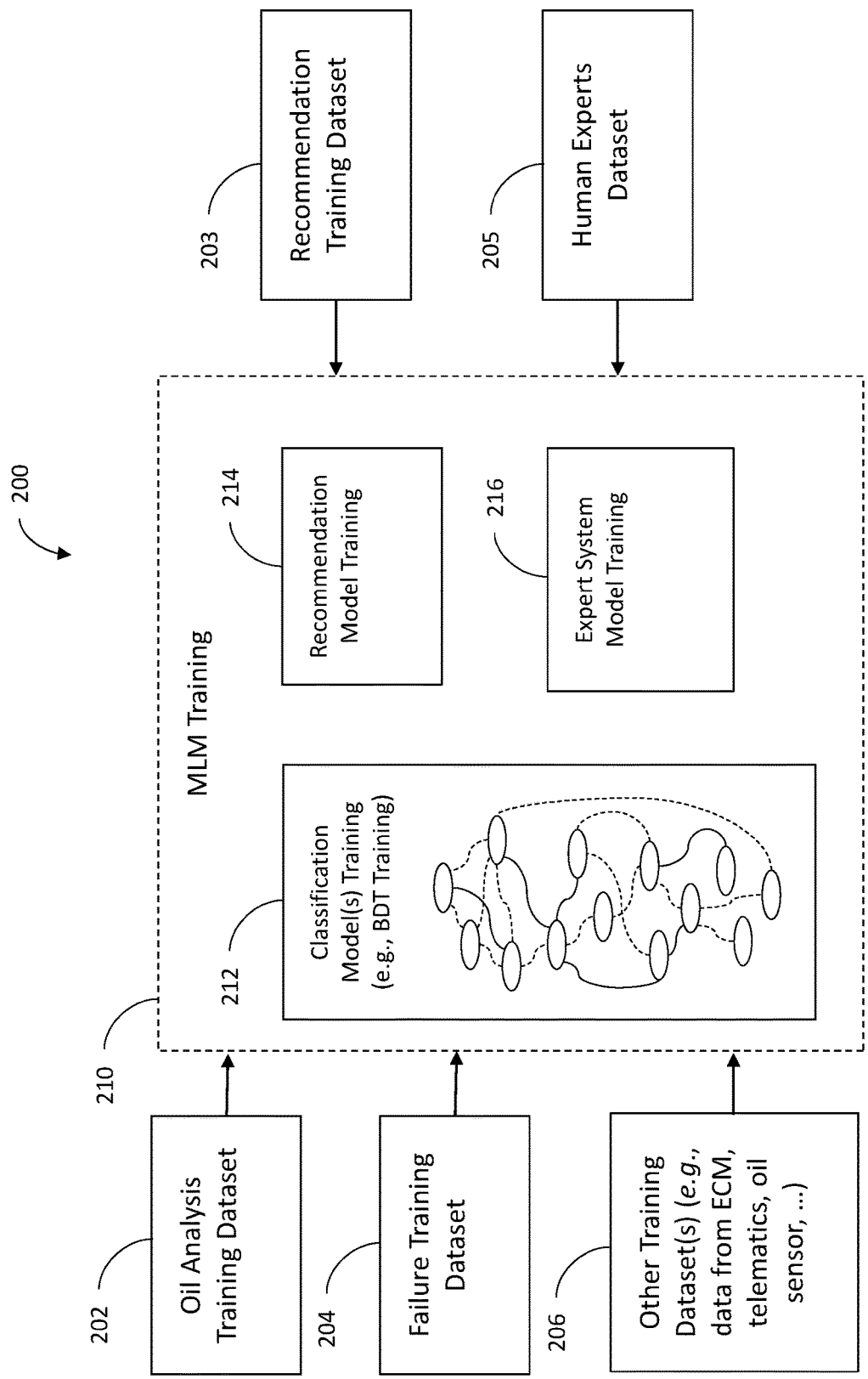
FIG. 2 is a schematic diagram illustrating certain aspects of an example predictive maintenance system.

With reference to FIG. 2, there are illustrated certain aspects of an example predictive maintenance system 200 undergoing a number of example machine learning model training operations 210. It shall be appreciated that the machine learning model training operations 210 described in connection with predictive maintenance system 200 may be utilized to configure, define, and/or provide the corresponding system components described above in connection with FIG. 1, including classification model(s) 104, recommendation model(s) 108, and expert system model 112. During the training operation, one or more classification model(s) 212 are trained using an oil analysis training dataset 202 and a failure training dataset 204. One or more other training datasets 206 may also be utilized training classification model(s) 212 including, for example, engine control module (ECM) data, telematics data, on-engine oil sensor data, or other on-engine sensor data. Such data may provide a variety of information about engine performance, such as fuel economy, percent idle, and other data.

Oil analysis training dataset 202 comprises values quantifying a plurality of chemical components measured use engine oil samples taken during oil change maintenance events for a plurality of engines of a common type or model. In the present example, the oil analysis training dataset 202 included approximately 248,000 data points and 38,000 records of the same engine type or model from engine oil changes over a three-year period. In the present example, each row or record of the dataset included values for engine identification (e.g., engine serial number), oil miles (engine mileage at the subject oil change), soot content, viscosity (e.g., kinematic viscosity at 100 C), Al content, Cr content, Cu content, Fe content, Pb content, Sn content, Ni content, Si content, Na content, and K content, as well as additional and alternate values indicating for other physical, elemental and/or chemical attributes, components, or properties measured in a sample of used oil taken from an engine. In this example, the engine serial number was utilized as the unique identifier that unites oil data with other datasets. The data points in the oil analysis training dataset 202 may be denoted $O_{i,j}$ corresponding to the i-th engine's j-th oil change.

Failure training dataset 204 comprises a set of engine failure codes indicating one of a plurality of predetermined failure types for the same plurality of engines and over a corresponding time period as oil analysis training dataset 202. Such information may be contained in or determined from maintenance and/or warranty data. In the present example, the failure training dataset 204 contained approximately 45,000 records or rows corresponded to the same engine population across the same three-year period as oil analysis training dataset 204. Each record or row includes values for engine identification (e.g., engine serial number), repair miles (engine mileage at the repair event), and fail code (e.g., an identifier denoting a specific component or system failure which was observed during an engine service or repair event associated with the failure event). The data points in the failure training dataset 204 may be denoted as $R_{i,k}$ corresponding to the i-th engine's k-th repair.

Since each oil analysis datapoint $O_{i,j}$ is not initially associated with a failure datapoint $R_{i,k}$, each oil analysis datapoint $O_{i,j}$ may be augmented by pairing with a failure datapoint $R_{i,k}$ of the same engine and each paired data point oil data point may be provided with additional information of a fail code, $f^o_{i,j}$, in accordance with Equation 1 below:

$$f^o_{i,j} = f_{i,k}, \text{ with } \min(m^r_{i,j} - m^o_{i,k}), (m^r_{i,j} - m^o_{i,k}) \geq 0 \quad \text{(Equation 1)}$$

In Equation 1 $m^r$ denotes repair miles, $m^o$ denotes oil miles, and $\min(m^r_{i,j} - m^o_{i,k})$ and $(m^r_{i,j} - m^o_{i,k}) \geq 0$ are pairing selection condition selecting the repair miles value with the minimum difference between repair miles and oil miles and repair miles greater than oil miles. It shall be appreciated that this is one example of identifying a given fail code relationship between oil or other data described in time by oil miles vs. fail code engine miles. Further examples may also associate all oil data before the fail code occurrence to generate the model instead of only the oil data preceding but closest to the fail code occurrence.

One or more of classification model(s) 212 may be trained to provide a two-class classification model, wherein the oil data with $f^o_{i,j} \neq$ null will be included in Class 1 (a failure observed with a fail code), while the ones with $f^o_{i,j} =$ null will be included in Class 0 (no failure observed). It is also contemplated that one or more of classification model(s) 212 may be trained to provide a higher order multiple-class classification model. A number of types of two-class classification models may be utilized including, for example, logistic regression, support vector machine, neural network, and boosted decision tree models. For certain applications, such as the present example, use of a two-class boosted decision tree (BDT) classification model provided unexpectedly preferred results. In the present example, each of classification model(s) 212 classifies one unique fail code, although, other examples may utilize higher-order multiple-class classification models.

Failure training dataset 204 included a plurality of instances of failure codes from an overall set of 500 possible unique fail codes. The most frequently occurring fail codes (e.g., the top 30, or another number or percentage defined as a cutoff or threshold) were selected and modeled with two-class classification models. The area under curve (AUC) for the resulting probability distributions were utilized to further select certain fail codes and their associated classification models. In the present example, fail code-based models with an AUC greater than 80% were selected for use in subsequent testing and evaluation operations, as shown in Table 1 below.

TABLE 1

| Failcode | # Instances | AUC |
|---|---|---|
| FC008 | 1048 | 0.977 |
| FC022 | 6482 | 0.960 |
| FC133 | 3629 | 0.928 |
| FC025 | 3561 | 0.891 |
| FC406 | 596 | 0.891 |
| FC073 | 1064 | 0.890 |

TABLE 1-continued

| Failcode | # Instances | AUC |
|---|---|---|
| FC014 | 238 | 0.880 |
| FC066 | 1051 | 0.863 |
| FC207 | 8319 | 0.857 |
| FC442 | 538 | 0.855 |
| FC058 | 1692 | 0.832 |
| FC109 | 666 | 0.819 |
| FC278 | 413 | 0.809 |
| FC328 | 591 | 0.807 |
| FC081 | 371 | 0.803 |
| FC209 | 460 | 0.801 |

Machine learning model training operations 210 may also include training of recommendation model 214. Based on the results of classification, the most possible fail code (or fail codes) that may happen prior to the next oil change can be identified. Furthermore, each fail code may have either correlational or causal relationships and they may happen in either a sequential or clustering fashion. Recommendation model 214 may be configured to model assessment using large scale online Bayesian recommendation technique to identify related items. To train and evaluate such a model, a new dataset is derived from the warranty dataset with the mapping defined in Equation 2.

$$\text{Engine ID} \rightarrow \text{User ID}, \text{Fail Code} \rightarrow \text{Item ID}, \#(\text{Fail Code}) \text{ for each (Engine ID, Fail Code)} \rightarrow \text{Rate} \quad \text{(Equation 2)}$$

Using the above training technique, recommendation model 214 was trained and configured to generate a related item table with 500+ rows. Each row has six columns for an item and its related items 1 to 5. The model's average normalized discounted cumulative gain (NDCG) was 0.95. Machine learning model training operations 210 may also include training of recommendation model 214.

Machine learning model training operations 210 may also include training of expert system 216 which is a computer-implemented system that emulates the decision-making ability of human experts. Expert system 216 is configured to solve complex problems by applying inference engine-based reasoning to a knowledge base with an if-then ruleset rather than through conventional procedural code. To configure and train expert system 216, several engine experts' knowledge was collected on the root cause of the top 16 fail code root causes discussed above in Table 1. The experts' knowledge of root causes was represented in the format of if-then rules. For example, for an asserted antecedent fail code ($f_i$) where i is an element of I ($i \in I$), against the inference engine which matches $\text{Rule}_k$, where k is an element of K ($k \in K$), that asserts a consequence (Cause) $c_j$, wherein j is an element of J ($j \in J$), $\text{Rule}_k$ can be expressed in accordance with Equation 3.

$$\text{Rule}_k: f_i \rightarrow c_j \quad \text{(Equation 3)}$$

In equation 3, I, J, and K ≤ 1. This process can also be referred to as forward chaining. To obtain the set of fail codes associated to the same cause, expert system 216 can use the backward chaining that states if the system is trying to determine if $c_j$ is true it would find $\text{Rule}_k$ among all k, $k \in K$, and query the knowledge base to see if any $f_i$, $i \in I$, is true.

Figure 3:
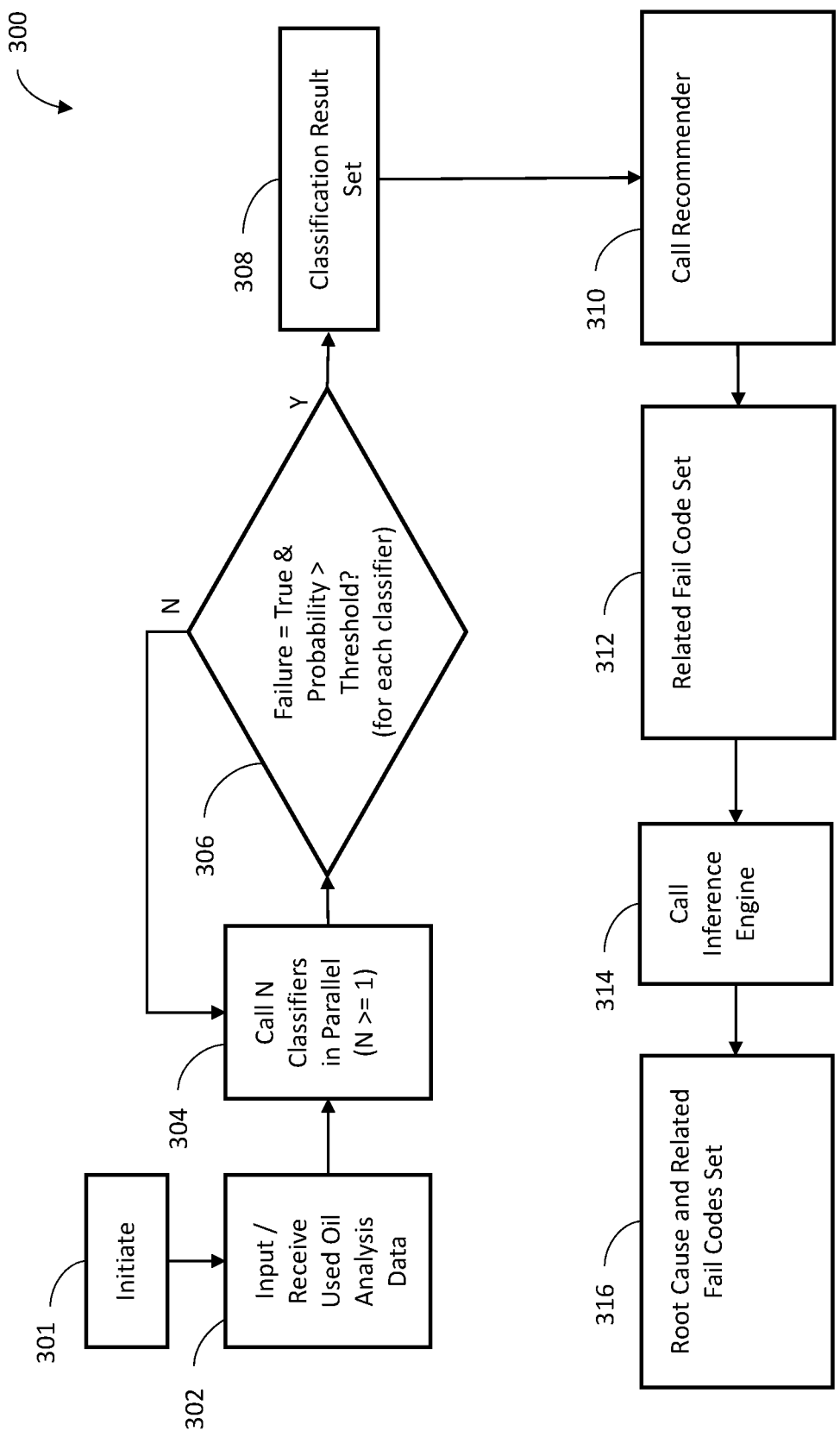
FIG. 3 is a flow diagram illustrating certain aspects of an example predictive maintenance process.

With reference to FIGS. 3 and 4, there are illustrated a flow diagram depicting certain aspects of an example predictive maintenance process 300 and a user interface display 400 which may be utilized in connection with process 300. Process 300 is initiated at operation 301 and proceeds to operation 302 where used oil analysis data is input to and received by a pre-trained predictive model. The used oil analysis data may include values quantifying a plurality of chemical components measured in a sample of used oil taken from an engine under analysis, for example, those described above in connection with system 100 or system 200. As illustrated in FIG. 4, the used oil analysis data may be displayed in table 410 of user interface display 400 or, additionally or alternatively, may be displayed as a graph, chart or other graphic on user interface display 400.

At operation 304, the pre-trained predictive model calls and initiates operation of one or more classification models (denoted as N Classifiers with N>=1), such as one or more of classification model(s) 104. The one or more classification models may be called, initiated, and executed in parallel, it being appreciated that sequential or serial operation and partially-sequential or partially serial operation are also possible. Operation 302 determines one or more fail code probabilities which are input to and received by conditional 306 which evaluates whether the received fail code is true and whether their probabilities are greater than an established threshold. The fail code probabilities for which conditional 306 true may be provided as classification result set 308 which may be displayed in a table 420 of user interface display 400 or, additionally or alternatively, may be displayed as a graph, chart or other graphic on user interface display 400.

One or more of the fail code probabilities included in classification result set 308 are provided to operation 310. The fail code probabilities provided to operation 310 may be selected based on a predetermined rule, such as the maximum probability, or based on user input, such as a selection of a probability on user interface display 400. Operation 310 calls and initiates operation of a recommendation model, such as recommendation model 108. The recommendation model performs an assessment to identify fail codes that are related to or adjacent to the one or more fail code corresponding provided to operation 310. The fail code and its related or adjacent fail codes may be provided as related fail code set 312 which may be displayed in a table 430 of user interface display 400 or, additionally or alternatively, may be displayed as a graph, chart or other graphic on user interface display 400.

Related fail code set 312 is provided to operation 314 which calls and initiates operation of an inference engine, such as an inference engine of expert system 112 or another expert system. The expert system 112 identifies one or more root causes in response to its received inputs which are provided as root cause and related fail codes set 316 and which may be which may be displayed in a tables 440 and 450 of user interface display 400 or, additionally or alternatively, may be displayed as a graph, chart or other graphic on user interface display 400. The expert system 112 may utilize the related items dataset to determine the root cause indicating the preventative maintenance action, for example, by determining a root cause corresponding to an item of the related item dataset or correlated with an item of the related item dataset.

Further description of a number of example embodiment is as follows. A first example embodiment is a method comprising: inputting used oil analysis data to a pre-trained predictive model, the used oil analysis data including values quantifying a plurality of chemical components measured in a sample of used oil taken from an engine under analysis; determining a probability of at least one fail code with the pre-trained predictive model in response to the used oil analysis data, the at least one fail code corresponding to one of a plurality of predetermined engine failure types; providing the at least one fail code and the probability of the at least one fail code to an expert system; performing with the expert system a root cause analysis of the at least one fail code to determine a root cause indicating a preventative maintenance action; and performing the predictive maintenance action on the engine under analysis.

A second example embodiment includes the features of the first example embodiment and comprises determining a related items dataset in response to the probability of the at least one fail code, the related items dataset including one or more other fail codes with a correlational or causal relationship to the at least one fail code; and providing the related items dataset to the expert system, wherein the expert system utilizes the related items dataset to determine the root cause indicating the preventative maintenance action.

A third example embodiment incudes the features of the first example embodiment, wherein the pre-trained predictive model includes one or more classification models. An additional form of the third example embodiment further includes the features of the second example embodiment.

A fourth example embodiment incudes the features of the third example embodiment, wherein the one or more classification models include a boosted decision tree model.

A fifth example embodiment incudes the features the first example embodiment, wherein the pre-trained predictive model is trained using an oil analysis training dataset including values quantifying a plurality of chemical components measured use engine oil samples taken during oil change maintenance events for a plurality of engines of a common type or model. An additional form of the fifth example embodiment further includes the features of the second example embodiment. An additional form of the fifth example embodiment further includes the features of the third example embodiment. An additional form of the fifth example embodiment further includes the features of the second example embodiment and the features of the third example embodiment. An additional form of the fifth example embodiment further includes the features of the third example embodiment and the features of the fourth example embodiment. An additional form of the fifth example embodiment further includes the features of the second example embodiment, the features of the third example embodiment and the features of the fourth example embodiment.

A sixth example embodiment incudes the features of the fifth example embodiment, wherein the pre-trained predictive model is trained using an engine failure training dataset comprising a set of engine failure codes indicating one of a plurality of predetermined failure types for said plurality of engines and over a corresponding time period as oil analysis training dataset.

A seventh example embodiment incudes the features of the first example embodiment, wherein the pre-trained predictive model is trained using an engine failure training dataset comprising a set of engine failure codes indicating one of a plurality of predetermined failure types for a plurality of engines.

An eighth example embodiment includes the features of any of the first through sixth example embodiments, wherein the expert system root cause analysis is configured to identify root causes of the fail codes using an inference engine which operates on a knowledge base represented by a ruleset of if-then rules.

An ninth example embodiment includes the features of any of the first through sixth example embodiments, wherein the expert system root cause analysis is performed using a forward chaining operation.

A tenth example embodiment includes the features of any of the first through sixth example embodiments, wherein the expert system root cause analysis is performed using a backward chaining operation.

An eleventh example embodiment is a system for predictive engine maintenance, the system comprising: a pre-trained predictive model component configured to receive an input including used oil analysis data and to determine a probability of at least one fail code in response to the used oil analysis data, the used oil analysis data including values quantifying a plurality of chemical components measured in a sample of used oil taken from an engine under analysis, the at least one fail code corresponding to one of a plurality of predetermined engine failure types; and an expert system model component configured to receive an input including the at least one fail code and the probability of the at least one fail code, perform a root cause analysis of the at least one fail code to determine a root cause, and in response to the root cause indicate a preventative maintenance action for the engine under analysis.

A twelfth example embodiment includes the features of the eleventh example embodiment and comprises a recommendation model component configured to determine a related items dataset in response to the probability of the at least one fail code, the related items dataset including one or more other fail codes with a correlational or causal relationship to the at least one fail code, wherein the expert system component is configured to receive the related items dataset and to determine the root cause indicating the preventative maintenance action.

A thirteenth example embodiment includes the features of the eleventh example embodiment, wherein the pre-trained predictive model component includes one or more classification models. An additional form of the thirteenth example embodiment further includes the features of the twelfth example embodiment.

A fourteenth example embodiment includes the features of the thirteenth example embodiment, wherein the one or more classification models include a boosted decision tree model.

A fifteenth example embodiment includes the features of the eleventh example embodiment, wherein the pre-trained predictive model component is trained using an oil analysis training dataset including values quantifying a plurality of chemical components measured use engine oil samples taken during oil change maintenance events for a plurality of engines of a common type or model. An additional form of the fifteenth example embodiment further includes the features of the twelfth example embodiment. An additional form of the fifth example embodiment further includes the features of the thirteenth example embodiment. An additional form of the fifth example embodiment further includes the features of the twelfth example embodiment and the features of the thirteenth example embodiment. An additional form of the fifth example embodiment further includes the features of the thirteenth example embodiment and the features of the fourteenth example embodiment. An additional form of the fifth example embodiment further includes the features of the twelfth example embodiment, the features of the thirteenth example embodiment and the features of the fourteenth example embodiment.

A sixteenth example embodiment includes the features of the fifteenth example embodiment, wherein the pre-trained predictive model component is trained using an engine failure training dataset comprising a set of engine failure codes indicating one of a plurality of predetermined failure types for said plurality of engines and over a corresponding time period as oil analysis training dataset.

A seventeenth example embodiment includes the features of the eleventh example embodiment, wherein the pre-trained predictive model component is trained using an engine failure training dataset comprising a set of engine failure codes indicating one of a plurality of predetermined failure types for a plurality of engines.

An eighteenth example embodiment includes the features of any of the eleventh through sixteenth example embodiments, wherein the expert system component configured to identify root causes of the fail codes using an inference engine which operates on a knowledge base represented by a ruleset of if-then rules.

An eighteenth example embodiment includes the features of any of the eleventh through sixteenth example embodiments, wherein the root cause analysis is performed using a forward chaining operation.

An eighteenth example embodiment includes the features of any of the eleventh through sixteenth example embodiments, wherein the root cause analysis is performed using a backward chaining operation.

While illustrative embodiments of the disclosure have been illustrated and described in detail in the drawings and foregoing description, the same is to be considered as illustrative and not restrictive in character, it being understood that only certain exemplary embodiments have been shown and described and that all changes and modifications that come within the spirit of the claimed inventions are desired to be protected. It should be understood that while the use of words such as preferable, preferably, preferred or more preferred utilized in the description above indicates that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A method comprising:
providing a computing system configured with a combination of models including a classification model pre-trained by machine learning to output one or more probabilities of one or more fail codes in response to input including oil analysis data, a recommendation model configured to receive output of the pre-trained classification model and pre-trained by machine learning to output a related items dataset in response to the one or more probabilities of one or more fail codes and, and an expert system model configured to receive output of the recommendation model and pre-trained by machine learning to output a root cause indicating a preventative maintenance action in response the related items dataset;
inputting used oil analysis data to the classification model, the used oil analysis data including values quantifying a plurality of chemical components measured in a sample of used oil taken from an engine under analysis;
determining a probability of at least one fail code with the classification model in response to the used oil analysis data, the at least one fail code corresponding to one of a plurality of predetermined engine failure types;

determining with the recommendation model a related items dataset in response to the at least one fail code;

providing the related items dataset, the at least one fail code and the probability of the at least one fail code to the expert system model;

determining a root cause indicating a preventative maintenance action with the expert system model in response to the related items dataset, the at least one fail code and the probability of the at least one fail code; and performing the predictive maintenance action on the engine under analysis.

2. The method of claim 1 wherein the related items dataset includes one or more other fail codes with a correlational relationship to the at least one fail code.

3. The method of claim 2 wherein wherein the related items dataset includes one or more other fail codes with a causal relationship to the at least one fail code.

4. The method of claim 1 wherein the models include classification model comprises a boosted decision tree model.

5. The method of claim 1 wherein the classification model is trained using an oil analysis training dataset including values quantifying a plurality of chemical components measured use engine oil samples taken during oil change maintenance events for a plurality of engines of a common type or model.

6. The method of claim 5 wherein the classification model is trained using an engine failure training dataset comprising a set of engine failure codes indicating one of a plurality of predetermined failure types for said plurality of engines and over a corresponding time period as oil analysis training dataset.

7. The method of claim 1 wherein the classification model is trained using an engine failure training dataset comprising a set of engine failure codes indicating one of a plurality of predetermined failure types for a plurality of engines.

8. The method of claim 1 wherein the expert system model is configured to identify root causes of the fail codes using an inference engine which operates on a knowledge base represented by a ruleset of if-then rules.

9. The method of claim 1 wherein the expert system model is configured to use a forward chaining operation.

10. The method of claim 1 wherein the expert system model is configured to use a backward chaining operation.

11. A system for predictive engine maintenance, the system comprising:

one or more computers configured to implement a combination of model components including a classification model component pre-trained by machine learning to output one or more probabilities of one or more fail codes in response to input including oil analysis data, a recommendation model component configured to receive output of the pre-trained classification model component and pre-trained by machine learning to output a related items dataset in response to the one or more probabilities of one or more fail codes and, and an expert system model component configured to receive output of the recommendation model component and pre-trained by machine learning to output a root cause indicating a preventative maintenance action in response the related items dataset, wherein the classification model component is configured to receive an input including used oil analysis data and to determine a probability of at least one fail code in response to the used oil analysis data, the used oil analysis data including values quantifying a plurality of chemical components measured in a sample of used oil taken from an engine under analysis, the at least one fail code corresponding to one of a plurality of predetermined engine failure types;

the recommendation model component is configured to determine a related items dataset in response to the at least one fail code; and the expert system model component is configured to receive an input including the related items dataset, the at least one fail code and the probability of the at least one fail code, perform a root cause analysis of the at least one fail code to determine a root cause in response to the related items dataset, the at least one fail code and the probability of the at least one fail code, and in response to the root cause indicate a preventative maintenance action for the engine under analysis.

12. The system of claim 11 wherein the related items dataset includes one or more other fail codes with a correlational relationship to the at least one fail code.

13. The system of claim 11 wherein the related items dataset includes one or more other fail codes with a causal relationship to the at least one fail code.

14. The system of claim 13 wherein the classification model component includes a boosted decision tree model.

15. The system of claim 11 wherein the classification model component is trained using an oil analysis training dataset including values quantifying a plurality of chemical components measured use engine oil samples taken during oil change maintenance events for a plurality of engines of a common type or model.

16. The system of claim 15 wherein the classification model component is trained using an engine failure training dataset comprising a set of engine failure codes indicating one of a plurality of predetermined failure types for said plurality of engines and over a corresponding time period as oil analysis training dataset.

17. The system of claim 11 wherein the classification model component is trained using an engine failure training dataset comprising a set of engine failure codes indicating one of a plurality of predetermined failure types for a plurality of engines.

18. The system of claim 11 wherein the expert system model component configured to identify root causes of the fail codes using an inference engine which operates on a knowledge base represented by a ruleset of if-then rules.

19. The system of claim 11 wherein the root cause analysis is performed using a forward chaining operation.

20. The system claim 11 wherein the root cause analysis is performed using a backward chaining operation.

* * * * *